United States Patent [19]

Sangokoya

[11] Patent Number: 5,371,260
[45] Date of Patent: Dec. 6, 1994

[54] AMINO-ALUMINOXANE COMPOSITIONS

[75] Inventor: Samuel A. Sangokoya, Baton Rouge, La.

[73] Assignee: Albemarle Corporation, Richmond, Va.

[21] Appl. No.: 179,171

[22] Filed: Jan. 10, 1994

[51] Int. Cl.$^5$ .............................................. C07F 5/06
[52] U.S. Cl. .................................... 556/171; 556/175; 556/176; 556/182; 556/187
[58] Field of Search ............... 556/175, 176, 182, 187, 556/171

[56] References Cited

U.S. PATENT DOCUMENTS 4,777,315 10/1988 Levine et al. ...................... 585/512

FOREIGN PATENT DOCUMENTS 0561476 9/1993 European Pat. Off. .
1319746 6/1973 United Kingdom .

OTHER PUBLICATIONS

JACS (1968), pp. 3173-3177, "The Partial Hydrolysis of Ethylalane Compounds", by Alan Storr et al.
JACS (1964), pp. 542-546, "Aluminum–Nitrogen Polymers by Condenstion Reactions", by A. W. Laubengayer et al.
Journal of Organometallic Chemistry, (1980), 186, 00 185–191, "Reactions of Tetraalkylaluminoxanes with Amines", by A. Piotrowski et al.
Polyhedron, (1990) vol. 9, No. 2/3, pp. 429–453, "Aluminoxanes: Synthesis, Structures, Complexes and Reactions", by S. Pasynkiewicz.

*Primary Examiner*—José G. Dees
*Assistant Examiner*—Porfirio Nazario-Gonzalez
*Attorney, Agent, or Firm*—David M. Bunnell

[57] ABSTRACT

Novel primary and secondary amino-aluminoxane derivatives are prepared by reacting an aluminoxane and a primary or secondary amine in an organic solvent, heating the reaction mixture to form a homogeneous solution and filtering the solution.

16 Claims, No Drawings

AMINO-ALUMINOXANE COMPOSITIONS

This invention relates generally to soluble aluminoxane derivatives and more particularly to amino-aluminoxane derivatives, obtained by the reaction of aluminoxanes with less than stoichiometric amounts of primary or secondary, aromatic, linear and cyclic amines, which in the presence of metallocenes form catalytically active compositions for olefin polymerization. The amino-aluminoxane compositions, after filtration, have greatly reduced trimethylaluminum concentration as well as improved clarity and solution stability.

Pasynkiewicz (Polyhedron (1990), 9, 429–453) describes the synthesis and characterization of amino-aluminoxane complexes with electron donor reagents. These reactions generally result in complex equilibrium products. Isolation of characterizable products from these reactions is often very difficult. Thus, a crystalline complex of tetramethylaluminoxane and N,N,N',N'-tetramethylethylenediamine (TMEDA) was obtained in 5–10% yield, by partial hydrolysis of trimethylaluminum (TMA) in TMEDA. Amines and ether complexes of aluminoxanes have been described, but they are usually unstable and decompose into the corresponding trialkylaluminum adduct, for example $Et_3Al$. THF and $Me_3Al.PhOMe$. In almost all of the aluminoxane complexes, only the tetraalkylaluminoxane adducts, having one or two Al—O—Al bonds are formed. These materials are usually inactive or have inferior activity, compared to the regular oligomeric aluminoxanes, in olefin oligomerization or polymerization.

A British patent 1,319,746 describes the hydrolysis of $R_3Al$ ($C_2$ to $C_4$) in tertiary amine solvent whereby the resulting aluminoxane contained no amine (or N atoms) after removal of the amine by distillation.

Pasynkiewicz et. al. (Journal of Organometallic Chemistry (1980), 186, 185–191) also reported the preparation of complexes of tetraalkylaluminoxanes with equimolar amounts of benzylamine and methylamine. The authors showed by spectroscopic methods that the reaction products consisted of mixtures of different isomeric trimers. These compounds are less active than methylaluminoxane in olefin polymerization.

Laubengayer et al. (J. Am. Chem. Soc., (1961), 83 542–546) have described the reactions of amines and amine hydrohalides with alkylaluminum compounds. Amines react with trialkylaluminum compounds to give different products. Thus, the reactions with tertiary, secondary and primary amines resulted in $R_3N$—$AlR_3$ adducts, $[R_2N$—$AlR_2]_2$ dimers and $[RN$—$AlR]_n$ oligomers respectively. Similarly, amine hydrohalides react with alkylaluminum compounds to give different products. The reactions of $R_3N.HX$ with $R_3Al$ and also that of $R_3N$ with $R_2AlX$ resulted in the same adduct product $R_3N$—$AlR_2X$. Secondary amines, $R_2NH$, react with $R_2AlX$ just as $R_2NH.HX$ reacts with $R_3Al$ to give the dimeric compound $[R_2N.AlRX]_2$. However, the reactions of primary amines lead to formation of oligomeric products. Thus, $RNH_2$ reacts with $R_2AlX$ and $RNH_2.HX$ reacts with $R_3Al$ to give the oligomer $[RNAlX]_n$ where $n > 3$.

Storr et al. (J. Am. Chem. Soc., (1968), 90, 3173–3177) discloses the reaction of $(EtAlCl_2)O$ with excess trimethylamine to form a 1:1 complex $(EtAlCl)_2.NMe_3$.

European Application 0,561,476 discloses polymethylaluminoxane compositions which are alleged to have increased solution stability in organic solvents, formed by reacting the polymethylaluminoxane with a $C_4$ or higher hydrocarbyl group-containing organic compound which contains an electron rich heteroatom. It further teaches the use of longer chain alkylamine compounds such as octylamine and decylamine, which are useful for better solubility but are rather deactivating in ethylene polymerization. Similarly, the application teaches the use of tertiary amines such as tri-n-octylamine and tridodecylamine for stabilizing aluminoxane solutions. These adduct compounds, at high polymerization temperature become very deactivating due to the lability of the adduct amine, which could block the polymerization site on the transition metal center.

The use of aluminoxanes in conjunction with metallocene compounds to oligomerize or polymerize olefin or olefinic compounds is well known. It is desirable to improve both the polymerization activity of the catalyst system and the quality of the polymer products. To this end, most research has exclusively focused on the modification of the metallocene compounds in order to effectuate the desired improvements. Examples of this endeavor are illustrated by U.S. Pat. Nos. 3,740,384, 4,945,076 and 5,034,549.

It is believed that the aluminoxane also has a major part to play in what happens during polymerization and it has now been discovered that the addition of an appropriate amount of amines to the aluminoxane improves the solubility of the aluminoxane with a concomitant improvement in the activity of the catalyst system. For example, within the limits of the appropriate amount of added amine, a 20 to 40 percent increase in polymer yield compared to regular MAO is observed. However, when certain limits ($\geq 20\%$, amine:Al molar value) of addition is exceeded, a marked reduction in activity is observed. Also, unless the product solution is filtered, the product solution is not stable. The product solutions of the invention are stable, clear and gel free and remain gel and precipitate free for over 4 months.

In accordance with this invention there is provided a process for preparing an amino-aluminoxane derivative which process comprises reacting an aluminoxane and from about 0.005 to less than about 0.2 mole, per mole of aluminum in said aluminoxane, of a primary or secondary amine in an organic solvent so as to form said derivative, heating the reaction mixture to form a homogeneous solution of said derivative and filtering said solution so as to remove gel forming materials from said derivative.

Also provided is a solution stable aminomethylaluminoxane composition in which the molar proportion of aluminum as trimethylaluminum in the initial methylaluminoxane is reduced from about 20–30% to about 4–15% in the amino-methylaluminoxane solution product.

Also provided are amino-methylaluminoxane compositions which when the solvent is completely removed are solid compositions containing minimal or no trimethylaluminum as determined by pyridine titration. Such a methylaluminoxane compositions, which have low trimethylaluminum concentrations and no significant reduction in potency when they are used as co-catalysts, are extremely valuable when used in conjunction with metallocene compositions which possess an easily reducible metal center such as titanium and the like. The lower trimethylaluminum content prevents or slows down the tendency for reduction of such centers during polymerization. Such reduction reactions are usually responsible for the decrease in activity and, therefore, limit the usefulness of certain catalyst systems especially at high temperature.

Preferred aluminoxanes for use in making the amino-aluminoxane derivatives are hydrocarbylaluminoxanes.

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl-(C_2H_5)_2$. The compounds preferred for use in olefin polymerization catalysts usually contain about 4 to 20 of the repeating units:

where R is $C_1$–$C_{10}$ alkyl and especially preferred are methylaluminoxanes (MAO). The methylaluminoxanes can contain some higher alkyl groups to improve their solubility. Such modified methylaluminoxanes which are included in the term "methylaluminoxane" as used herein are described, for example, in U.S. Pat. Nos. 5,157,008 and 5,066,631. Besides MAO, nonlimiting examples of hydro-carbylaluminoxanes for use in the invention include ethylaluminoxanes (EAO), isobutylaluminoxanes (IBAO), n-propylaluminoxanes, n-octylaluminoxanes, and the like.

The aluminoxanes can be prepared as known in the art by the partial hydrolysis of trialkylaluminum compounds. The trialkylaluminoxane compounds can be hydrolyzed by adding either free water or water containing solids, which can be either hydrates or porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4.5H_2O$, $Al_2(SO_4)_3.18H_2O$, $FeSO_4.7H_2O$, $AlCl_3.6H_2O$, $Al(NO_3)_3.9H_2O$, $MgSO_4.7H_2O$, $ZnSo_4.7H_2O$, $Na_2SO_4.10H_2O$, $Na_3PO_4.12H_2O$, $LiBr.2H_2O$, $LiCl.1H_2O$, $LiI.2H_2O$, $LiI.3H_2O$, $KF.2H_2O$, $NaBr.2H_2O$ and the like and alkali or alkaline earth metal hydroxides such as, for example, $NaOH.H_2O$, $NaOH.2H_2O$, $Ba(OH)_2.8H_2O$, $KOH.2H_2O$, $CsOH.1H_2O$, $LiOH.1H_2O$ and the like. Mixtures of any of the above hydrates can be used. The mole ratios of free water or water in the hydrate or in porous materials such as alumina or silica to total alkyl aluminum compounds in the mixture can vary widely, such as for example from about 2:1 to 1:4 with ratios of from about 4:3 to 1:3.5 being preferred.

Such processes for preparing hydrocarbylaluminoxanes are described, for example, in U.S. Pat. No. 4,908,463. The methylaluminoxanes contain varying amounts, of from about 5 to 35 mole percent, of the aluminum value as unreacted trimethylaluminum.

Amines for use in the invention are mono and polydentate primary and secondary amines. Such amines include acyclic, cyclic and macrocyclic aliphatic amines and aromatic amines which contain from 1 to 20 carbon atoms and 1 to 4 amino groups and, preferably, from 1 to 6 carbon atoms and 1 or 2 amino groups.

Non-limiting examples of specific amines are methylamine, dimethylamine, ethylamine, diethylamine, propylamine, dipropylamine, isopropylamine, diisopropylamine, butylamine, dibutylamine, isobutylamine, diisobutylamine, cyclohexylamine, dicyclohexylamine, ethyl-n-butylamine, ethylenediamine, propylenediamine, octanamine, dodecanamine, octadecanamine, piperazine, morpholine, cyclam, aniline, N-methylaniline, phenylaniline, 2-ethylaniline, N-ethylaniline, diphenylamine, toluidene, xylidines, methylenedianiline, and the like.

The amino-aluminoxanes can be prepared by reacting the aluminoxane and amine in an organic solvent in molar proportions of amine (N) of from about 0.005 to less than about 0.2 mole per mole of aluminum in the aluminoxane and preferably from about 0.01 to 0.15 mole of amine per mole of aluminum. Amounts of 0.2 mole per mole have reduced polymerization activity compared with untreated aluminoxane. Mixtures of aluminoxanes and/or mixtures of amines can be used in forming the derivatives. Any inert organic solvent can be used as the reaction medium. Non-limiting examples of solvents include aliphatic hydrocarbons such as pentane, isopentane, hexane, cyclohexane, heptane, octane, decane, dodecane, hexadecane, octadecane and the like with those having carbon numbers of 5 to 10 being preferred and aromatic hydrocarbons such as benzene, toluene, xylene, cumene and the like with those having carbon numbers of 6 to 20 being preferred. Generally amounts of solvent to provide a total concentration of reactants of from about 2 to 30 wt. percent are used.

For commercial purposes, it would be more profitable to minimize any extraneous processing procedures such as heating, filtration, agitation and the like. Therefore, a simple addition of the amine to the methylaluminoxane solution without further processing would be preferable. However, Comparison Example 5 below shows the importance of the filtration step after treatment of the MAO solution with the amine clarifying agent. When the filtration step was omitted, the gelation process restarted within a couple of weeks and got worse with time. Therefore, it appears that the filtration step effectively caused the removal of any gel forming materials in the methylaluminoxane solution and thus prevent the reoccurrence of the gelation process.

Additionally, it should be noted, however, that ordinarily it is difficult to filter methylaluminoxane solutions without previous appropriate treatments such as those described herein. Furthermore, the heating process, as described herein, is necessary in order to convert the immediate product, which is indicated by the presence of clathrate formation (immiscible liquid layers), to the final stable, clear and homogeneous aminomethylaluminoxane solution.

Although the aliphatic amine reagents are very useful for the clarification of cloudy and gelatinous methylaluminoxane solutions, as the total carbon number becomes larger ($C_4$ and above), a gradual reduction in the activity of the resulting products occur when they are used as co-catalyst in ethylene polymerization. Therefore, it appears that there is a trade off between the effectiveness of the amines as clarifying or stabilizing agents and/or activity improvers. According to the present clarification procedure as described herein, amines with carbon numbers equal or less than 6 appear to be more effective both as clarifying agents and as activity improvers, while those with larger carbon numbers are more suitable for enhanced clarification with a concomitant reduction in activity.

Preferred reaction temperatures range from about 25° to 125° C. with the reaction mixture having been heated to at least about 80° C. at some time prior to the filtration step in order to provide clear, single phase solutions of amino-aluminoxane derivatives at concentrations of up to about 30 weight percent.

The amino-aluminoxanes can be used in combination with metallocenes to provide olefin polymerization catalysts. Such metallocenes are well known in the art and non-limiting examples include the metallocenes of Groups 3, 4, 5, 6, lathanide and actinide metals such as the metallocenes of transition metals which are described in published European patent application No. 0 129,368 and U.S. Pat. Nos. 5,017,714, 5,026,798 and 5,036,034, whose teachings with respect to such metallocenes are incorporated herein by reference. Illustrative examples of such metallocenes are bis-(cyclopentadienyl)zirconium dimethyl, bis(cyclopentadienyl)zirconium dichloride, bis-(cyclopentadienyl)zirconium monomethylmonochloride, bis-(cyclopentadienyl)-titanium dichloride, bis-(cyclopentadienyl)-titanium difluoride, cyclopentadienylzirconium tri-(2-ethylhexanoate), bis-cyclopentadienyl)zirconium hydrogen chloride, bis-(cyclopentadienyl)hafnium dichloride and the like.

The catalyst components are used in proportions to provide mole ratios of metal atom in the metallocene to aluminum atom in the amino-aluminoxane of from about 0.0002:1 to 0.2:1 and preferably 0.0005:1 to 0.02:1. The catalyst components can be used in solution or deposited on a solid support. The solid support can be any particulate solid, and particularly porous supports such as talc or inorganic oxides, or resinous support material such as polyolefins. Preferably, the support material is an inorganic oxide in finely divided form.

Suitable inorganic oxide support materials which are desirably employed include Group IIA, IIIA, IVA or IVB metal oxides such as silica, alumina, silica-alumina and mixtures thereof. Other inorganic oxides that may be employed either alone or in combination with the silica, alumina or silica-alumina are magnesia, titania, zirconia, and the like. Other suitable support materials are finely divided polyolefins such as finely divided polyethylene.

The catalysts are effective to produce olefin polymers and especially ethylene polymers and ethylene/α-olefin copolymers. Examples of olefins that can be polymerized in the presence of the catalysts of the invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Polymerization of ethylene or copolymerization with ethylene and an α-olefin having 3 to 10 carbon atoms is preferable. Such polymerizatons may be performed in either the gas, slurry or liquid phase (e.g. in a solvent, such as toluene, or in a diluent, such as heptane). The polymerization can be conducted at conventional temperatures (e.g., 0° to 120° C.) and pressures (e.g., ambient to 50 kg/cm$^2$) using conventional procedures as to molecular weight regulations and the like.

The invention is further illustrated by, but is not intended to be limited to, the following examples. The procedures of the examples were carried out under inert atmosphere conditions, using Schlenk glassware and vacuum line, in conjunction with a $N_2$-drybox. Solvents were distilled using standard methods. Filtration and vacuum distillation were done inside a $N_2$-drybox and distillates were collected in a trap at $-78°$ C. The amine reagents were purchased from a commercial source and were used as received. Aluminoxanes were obtained from stock solutions produced by Ethyl Corporation. Methylaluminoxane (MAO) solutions typically contain about 50% of the aluminum value as trimethylaluminum (TMA) with preferred samples having only 20–30% of contained aluminum value as TMA as determined by pyridine titration.

Example 1

A 10 wt % toluene solution of methylaluminoxane (MAO, 254 mmol Al ) was placed in a reaction flask inside a $N_2$-drybox. Isopropylamine (0.3 g, 5.1 mmol) dissolved in toluene (6 g) was slowly added via a syringe during a period of about 15 minutes. The mixture was stirred at room temperature for about 30 minutes. Dissolved gas was allowed to escape. The reaction flask was then heated (oil bath) at 80° C. for two hours. The initially cloudy MAO solution became clearer.

The solution product was initially filtered through a coarse frit by gravity and then was easily filtered through a medium frit. After filtration, the solution remained clear and gel-free even after four months. The final product contained 206 mmol of Al, which is 81% of the initial aluminum value. Some of the liquid product was concentrated under vacuum to give a free flowing, colorless solid product. The product is found to be somewhat more active in ethylene polymerization than regular MAO. Product analyses are shown in Table 1.

Example 2

MAO solution in toluene (91 g, 154 mmol Al) was placed in a reaction flask. Isopropylamine (0.5 g, 7.7 mmol) was added dropwise from a syringe. Some gas evolution was noticed. Obvious clarification of the cloudy MAO solution occurred. After addition, the mixture was stirred at room temperature during a period of one hour. The appearance of a small immiscible lower layer (clathrate formation) was noted. The mixture was then heated (oil bath) at 80° C. for about two hours to give a clear, homogeneous liquid product.

Filtration through a medium frit was fairly easy and residue was negligible. Analysis showed the recovery of about 97% of the original aluminum value. The solution remained gel free even after 6 months and remained very active in ethylene polymerization.

A portion of the liquid product was concentrated to dryness to give a free-flowing solid aminomethyl-aluminoxane which contained minimal or no aluminum value as trimethylaluminum (less than 2 mole %) as determined by pyridine titration.

Example 3

Isopropylamine (1.44 g, 24.3 mmol) was allowed to react with MAO solution in toluene (143 g, 243 mmol Al) as described in Example 2. Clarification and gas evolution were observed. Additionally, a small clathrate formation (immiscible liquid) was also observed. The mixture was stirred overnight at room temperature and then heated (oil bath) at 80° C. for about 3 hours. On cooling, the clear, homogeneous solution was filtered through a medium frit. A quantitative recovery of the original aluminum value (>99%) was obtained. The product was found to be active in ethylene polymerization. The solid product obtained by vacuum distillation to remove the solvent was shown to contain minimal or no trimethylaluminum by pyridine titration.

Comparison 1

While stoichiometric or near stoichiometric addition of amines to MAO solution resulted in clarification of the solution, the reaction product is strongly deactivating in ethylene polymerization. Thus, MAO solution (140 g, 238 mmol Al) was treated with isopropylamine (2.8 g, 47 mmol) as described in example 3. Clathrate formation disappeared after heating. The clear homogeneous solution was filtered through medium frit to give a quantitative recovery of the original aluminum value. This material exhibited a drastic reduction of activity in ethylene polymerization as shown in Table 2.

Example 4

Isobutylamine (0.9 g, 12.1 mmol) was allowed to react with MAO solution in toluene (143 g, 243 mmol Al) as described in Example 2. After filtration through a medium frit, a clear, gel free solution resulted. The final reaction product contained 99% of the original aluminum value. No signs of gelation was observed after 6 months. The product was very active in ethylene polymerization when used in conjunction with zirconocene dichloride.

Example 5

Isobutylamine (1.8 g, 24.3 mmol) was added to a solution of MAO in toluene (143 g, 243 mmol Al). The reaction was carried out as described in Example 2. A clear, homogeneous reaction product resulted. Filtration through a medium frit was easy. The product showed great stability to gel formation and is active in ethylene polymerization.

Comparison 2

As the N/Al mole ratio of the reactants amine/MAO approaches 0.2 or greater, a drastic reduction of the activity in ethylene polymerization is observed. Isobutylamine derivatives also follow this trend. Thus, isobutylamine (3.1 g, 42 mmol) was allowed to react with MAO solution in toluene (124 g, 211 mmol Al) as described in Example 2. After filtration, a clear gel free solution resulted. While this product showed great stability, it behaved poorly in ethylene polymerization.

Example 6

MAO (141 g, 240 mmol Al) was treated with aniline (1.12 g, 12 mmol) as described for Example 2. Filtration was slightly more difficult. However, a clear, gel free solution resulted. The solution remained clear with no sign of gelation even after 4 months.

Example 7

Aniline (2.25 g, 24 mmol) was added slowly to MAO solution (142 g, 241 mmol Al) at room temperature inside a $N_2$-drybox. The reaction was worked out as described in Example 2. Filtration was slightly less difficult compared to Example 6. The product was found to be active in ethylene polymerization.

Comparison 3

This comparison also demonstrates that aminoaluminoxane products become less active as the mole ratio N/Al of the reactants, aniline/MAO, approaches or exceeds 0.2. Aniline (4.5 g, 48 mmol) was allowed to react with MAO (141 g, 240 mmol) as described in Example 2. Filtration through a medium frit was easy compared to Examples 6 and 7. The product showed great stability over a 6 months period. However, the activity in ethylene polymerization was significantly reduced.

Example 8

Examples 8 and 9 demonstrate that secondary aliphatic amines behave exactly as both primary and aromatic amines. Treatment of a MAO solution (66.1 g, 132.2 mmol Al) with diisopropylamine (0.7 g, 6.6 mmol) as described in Example 2 resulted in a clear, colorless liquid product after filtration. The gel free solution was active in ethylene polymerization.

Example 9

To a solution of MAO in toluene (93.7 g, 384 mmol Al) was added diisopropylamine (5.8 g, 58 mmol) and the reaction carried out as described in Example 2. The mixture was relatively easy to filter through medium frit. After filtration, clear non-gelatinous solution was obtained. The solution remained stable even after 6 months. The product showed moderate activity in ethylene polymerization.

Comparison 4

This comparison again demonstrates that as the mole ratio of N/Al was increased a significant drop in activity was observed. MAO (118 g, 236 mmol Al) was treated with diisopropylamine (4.8 g, 47 mmol) as described in Example 2. Instant clarification was observed even before heating. Filtration through a medium frit was very easy. The product remained gel free even after 6 months, but behaved rather poorly in ethylene polymerization.

Comparison 5

From the commercial point of view, it would be more profitable to minimize processing such as heating, filtration and the like. Therefore, a simple addition of the amine to the methylaluminoxane solution without further processing would be preferable.

A 10 wt % toluene solution of methylaluminoxane (MAO, 254 mmol Al) was allowed to react with isopropylamine (0.3 g, 5.1 mmol) as described in Example 1. The initially cloudy MAO solution became clearer. The reaction product was not filtered, but stored under $N_2$ in a dry box. Within two weeks a thin, fine gelatinous layer started to form at the bottom of the flask. During prolonged storage, more and more gel formation was observed. During the same storage period and conditions, no gel formation was noticed in the reaction product of Example 1, which was carried out exactly as Comparison 5 except that the reaction mixture was filtered before storage.

This comparison shows the importance of the appropriate work-up procedure after treatment of the MAO solution with amine reagents as described herein. Furthermore, the heating process is necessary in order to convert the intermediate product, which indicates the presence of clathrate formation (immiscible liquid layers), to the final stable, clear, and homogeneous aminoaluminoxane solution.

Example 10—Polymerization of Ethylene

Reaction products from the above described examples were used in conjunction with zirconocene dichloride to polymerize ethylene.

Inside a $N_2$-drybox, an autoclave (600 ml) was charged with toluene (250 ml). A mixture of the aminoaluminoxane product and zirconocene dichloride ($6.8 \times 10^{-6}$ mol) in toluene (50 ml) was added. Then the autoclave was brought out and set up in a hood. The reactor was heated to 90° C. and then ethylene was introduced at 60 psi during 10 minutes. The reaction was quenched by addition of methanol (300 ml). The polyethylene produced was initially air dried, followed by drying in a vacuum oven without heating. Yields of polyethylene and activities of the catalyst compositions are reported in Table 2.

TABLE 1

Amino-aluminoxane Derivatives Product Analysis

| Examples | Amine/Al Mole Ratio | Filtration$^c$ (Medium Frit) | Soluble Aluminum Recovered (%) | $TMA^a$ Content % | Stability$^b$ (Months) |
|---|---|---|---|---|---|
| Regular MAO | — | V. Difficult | 60 | 26 | <1 |
| Example 1 | 0.02 | S. Difficult | 81 | — | >6 |
| Example 2 | 0.05 | F. Easy | 97 | 14.0 | >6 |
| Example 3 | 0.10 | Easy | 99 | 11.0 | >6 |
| Comparison 1 | 0.20 | V. Easy | 99 | 5.1 | >6 |
| Example 4 | 0.05 | F. Easy | 99 | 14.3 | >6 |
| Example 5 | 0.10 | Easy | 99 | 11.4 | >6 |
| Comparison 2 | 0.20 | V. Easy | 99 | 3.4 | >6 |
| Example 6 | 0.05 | S. Difficult | 95 | 15.4 | >6 |
| Example 7 | 0.10 | Easy | 96 | 11.6 | >6 |
| Comparison 3 | 0.20 | V. Easy | 99 | 4.8 | >6 |
| Example 8 | 0.05 | Difficult | 85 | — | >6 |
| Example 9 | 0.10 | S. Difficult | 89 | — | >6 |
| Comparison 4 | 0.20 | S. Difficult | 92 | — | >6 |

$^a$Mole % Al as TMA, determined by pyridine titration.
$^b$Time elapsed before the appearance of gel or precipitates.
$^c$F = faily; S = slightly; V = very

TABLE 2

Ethylene Polymerization Test$^a$ Amino-aluminoxane Derivatives

| MAO Composition | Zirconocene Dichloride (Moles × $10^{-6}$) | Al/Zr Mole Ratio | Activity (× $10^6$) g (PE)/Mole Zr.atm.hr | Activity Compared to Regular MAO | Polyethylene (g) |
|---|---|---|---|---|---|
| Regular MAO$^b$ | 6.8 | 1470 | 6.70 | 1.0 | 31 |
| Example 1 | 6.8 | 1470 | 9.51 | 1.42 | 44 |
| Example 2 | 6.8 | 1470 | 9.95 | 1.48 | 46 |
| Example 3 | 6.8 | 1470 | 8.43 | 1.26 | 39 |
| Comparison 1 | 6.8 | 1470 | 4.32 | 0.65 | 20 |
| Example 4 | 6.8 | 1470 | 9.51 | 1.42 | 44 |
| Example 5 | 6.8 | 1470 | 8.22 | 1.23 | 38 |
| Comparison 2 | 6.8 | 1470 | 3.46 | 0.52 | 16 |
| Example 6 | 6.8 | 1470 | 9.95 | 1.48 | 46 |
| Example 7 | 6.8 | 1470 | 8.87 | 1.32 | 41 |
| Comparison 3 | 6.8 | 1470 | 3.89 | 0.58 | 18 |
| Example 8 | 6.8 | 1470 | 9.51 | 1.42 | 44 |
| Example 9 | 6.8 | 1470 | 6.48 | 0.97 | 30 |
| Comparison 4 | 6.8 | 1470 | 3.24 | 0.48 | 15 |

$^a$Conducted at 60 psi ethylene, 90° C., in toluene (300 ml) for 10 minutes.
$^b$Control experiment using untreated MAO solution.

What is claimed is:

1. A process for preparing an amino-aluminoxane derivative, said process comprising reacting an aluminoxane and from about 0.005 to less than about 0.2 mole, per mole of aluminum in said aluminoxane, of a primary or secondary amine in an organic solvent so as to form said derivative, heating the reaction mixture to form a homogeneous solution of said derivative, and filtering said solution so as to remove gel forming materials from said derivative.

2. The process of claim 1 wherein from about 0.01 to about 0.15 mole of amine per mole of aluminum in said aluminoxane is reacted.

3. The process of claim 1 wherein the amine is selected from the group consisting of acyclic, cyclic, macrocyclic aliphatic amines having from 1 to 20 carbon atoms and 1–4 amino groups and aromatic amines having from 6 to 20 carbon atoms and 1 to 4 amino groups and the aluminoxane is a methylaluminoxane.

4. The process of claim 3 wherein the amine is selected from the group consisting of methylamine, dimethyl amine, ethylamine, diethylamine, propylamine, dipropylamine, isopropylamine, diisopropylamine, butylamine, dibutylamine, isobutylamine, diisobutylamine, aniline and phenylaniline.

5. The process of claim 1 including the step of removing the organic solvent from said filtered solution so as to recover said derivative as a solid.

6. The process of claim 1 wherein the amine contains 1 to 6 carbon atoms and 1 or 2 amine groups.

7. The process of claim 6 wherein said amine is isopropyl amine.

8. The process of claim 1 wherein said aluminoxane is selected from the group consisting of methylaluminoxane, ethylaluminoxane, isobutylaluminoxane, n-octylaluminoxane and mixtures thereof.

9. An organic solvent soluble amino-aluminoxane composition prepared by the process which comprises reacting an aluminoxane and from about 0.005 to less than about 0.2 mole, per mole of aluminum in said aluminoxane, of a primary or secondary amine in an organic solvent so as to form said composition, heating the reaction mixture to form a homogeneous solution of said composition, and filtering said solution so as to remove gel forming materials from said composition.

10. The composition of claim 9 wherein from about 0.01 to about 0.15 mole of amine per mole of aluminum in said aluminoxane is reacted.

11. The composition of claim 9 wherein the amine is selected from the group consisting of acyclic, cyclic, macrocyclic aliphatic amines having from 1 to 20 carbon atoms and 1–4 amino groups and aromatic amines having from 6 to 20 carbon atoms and 1 to 4 amino groups and the aluminoxane is a methylaluminoxane.

12. The composition of claim 11 wherein the amine is selected from the group consisting of methylamine, dimethyl amine, ethylamine, diethylamine, propylamine, dipropylamine, isopropylamine, diisopropylamine, butylamine, dibutylamine, isobutylamine, diisobutylamine, aniline and phenylaniline.

13. The composition of claim 9 wherein the amine contains 1 to 6 carbon atoms and 1 or 2 amine groups.

14. The composition of claim 9 wherein said amine is isopropyl amine.

15. The composition of claim 9 wherein the aluminoxane reactant is methylaluminoxane and the molar percentage of aluminum as trimethylaluminum in said methylaluminoxane is reduced from a starting value of from about 20 to 30 mole % in said methylaluminoxane to a value of from about 4 to 15 mole % in said composition.

16. The composition of claim 9 wherein the solvent is removed from the filtered solution to provide a solid amino-methylaluminoxane composition which contains less than about 2 mol % aluminum as trimethylaluminum.

* * * * *